US00RE36041E

United States Patent [19]

Turk et al.

[11] E Patent Number: Re. 36,041

[45] Reissued Date of Patent: Jan. 12, 1999

[54] FACE RECOGNITION SYSTEM

[75] Inventors: Matthew Turk; Alex P. Pentland, both of Cambridge, Mass.

[73] Assignee: Massachusetts Institute of Technology, Cambridge, Mass.

[21] Appl. No.: 340,615

[22] Filed: Nov. 16, 1994

Related U.S. Patent Documents

Reissue of:

[64] Patent No.: 5,164,992
Issued: Nov. 17, 1992
Appl. No.: 608,000
Filed: Nov. 1, 1990

[51] Int. Cl.[6] ..... G06K 9/00

[52] U.S. Cl. ..... 382/118; 358/84; 382/201; 382/204; 455/2

[58] Field of Search ..... 382/115, 118, 382/200, 201, 195, 278, 279, 724, 204; 348/143, 1; 340/825.36, 825.49; 455/2

[56] References Cited

U.S. PATENT DOCUMENTS

| | | | |
|---|---|---|---|
| 4,636,862 | 1/1987 | Hatori et al. | 358/105 |
| 4,651,289 | 3/1987 | Maeda et al. | 382/15 |
| 4,752,957 | 6/1988 | Maeda | 382/36 |
| 4,838,644 | 6/1989 | Ochoa et al. | 382/42 |
| 4,858,000 | 8/1989 | Lu | 382/2 |
| 4,926,491 | 5/1990 | Maeda et al. | 382/36 |
| 4,930,011 | 5/1990 | Kiewit | 358/84 |
| 4,998,286 | 3/1991 | Tsujiuchi et al. | 382/42 |
| 5,031,228 | 7/1991 | Lu | 358/84 |

OTHER PUBLICATIONS

L. Sirovich et al., 1987 Optical Society of America, "Low-dimensional procedure for the characterization of human faces", pp. 519–524.

*Primary Examiner*—Joseph Mancuso
*Attorney, Agent, or Firm*—Fish & Richardson, P.C.

[57] ABSTRACT

A recognition system for identifying members of an audience, the system including an imaging system which generates an image of the audience; a selector module for selecting a portion of the generated image; a detection means which analyzes the selected image portion to determine whether an image of a person is present; and a recognition module responsive to the detection means for determining whether a detected image of a person identified by the detection means resembles one of a reference set of images of individuals.

37 Claims, 1 Drawing Sheet

FACE RECOGNITION SYSTEM

Matter enclosed in heavy brackets [ ] appears in the original patent but forms no part of this reissue specification; matter printed in italics indicates the additions made by reissue.

BACKGROUND OF THE INVENTION

The invention relates to a system for identifying members of a viewing audience.

For a commercial television network, the cost of its advertising time depends critically on the popularity of its programs among the television viewing audience. Popularity, in this case, is typically measured in terms of the program's share of the total audience viewing television at the time the program airs. As a general rule of thumb, advertisers prefer to place their advertisements where they will reach the greatest number of people. Thus, there is a higher demand among commercial advertisers for advertising time slots along side more popular programs. Such time slots can also demand a higher price.

Because the economics of television advertising depends so critically on the tastes and preferences of the television audience, the television industry invests a substantial amount of time, effort and money in measuring those tastes and preferences. One preferred approach involves monitoring the actual viewing habits of a group of volunteer families which represent a cross-section of all people who watch television. Typically, the participants in such a study allow monitoring equipment to be placed in their homes. Whenever a participant watches a television program, the monitoring equipment records the time, the identity of the program and the identity of the members of the viewing audience. Many of these systems require active participation by the television viewer to obtain the monitoring information. That is, the viewer must in some way interact with the equipment to record his presence in the viewing audience. If the viewer forgets to record his presence the monitoring statistics will be incomplete. In general, the less manual intervention required by the television viewer, the more likely it is that the gathered statistics on viewing habits will be complete and error free.

Systems have been developed which automatically identify members of the viewing audience without requiring the viewer to enter any information. For example, U.S. Pat. No. 4,858,000 to Daozehng Lu, issued Aug. 15, 1989 describes such a system. In the system, a scanner using infrared detectors locates a member of the viewing audience, captures an image of the located member, extracts a pattern signature for the captured image and then compares the extracted pattern signature to a set of stored pattern image signatures to identify the audience member.

SUMMARY OF THE INVENTION

In general, in one aspect, the invention is a recognition system for identifying members of an audience. The invention includes an imaging system which generates an image of the audience; a selector module for selecting a portion of the generated image; a detection means which analyzes the selected image portion to determine whether an image of a person is present; and a recognition module for determining whether a detected image of a person resembles one of a reference set of images of individuals.

Preferred embodiments include the following features. The recognition module also determines which one, if any, of the individuals in the reference set the detected image resembles. The selection means includes a motion detector for identifying the selected portion of the image by detecting motion and it includes a locator module for locating the portion of the image corresponding to the face of the person detected. In the recognition system, the detection means and the recognition module employ a first and second pattern recognition techniques, respectively, to determine whether an image of a person is present in the selected portion of the image and both pattern recognition techniques employ a set of eigenvectors in a multi-dimensional image space to characterize the reference set. In addition, the second pattern recognition technique also represents each member of the reference set as a point in a subspace defined by the set of eigenvectors. Also, the image of a person is an image of a person's face and the reference set includes images of faces of the individuals.

Also in preferred embodiments, the recognition system includes means for representing the reference set as a set of eigenvectors in a multi-dimensional image space and the detection means includes means for representing the selected image portion as an input vector in the multi-dimensional image space and means for computing the distance between a point identified by the input vector and a subspace defined by the set of eigenvectors. The detection means also includes a thresholding means for determining whether an image of a person is present by comparing the computed distance to a preselected threshold. The recognition module includes means for representing each member of the reference set as a corresponding point in the subspace. To determine the location of each point in subspace associated with a corresponding member of the reference set, a vector associated with that member is projected onto the subspace.

The recognition module also includes means for projecting the input vector onto the subspace, means for selecting a particular member of the reference set, and means for computing a distance within the subspace between a point identified by the projection of the input vector onto the subspace and the point in the subspace associated with the selected member.

In general, in another aspect, the invention is a method for identifying members of an audience. The invention includes the steps of generating an image of the audience; selecting a portion of the generated image; analyzing the selected image portion to determine whether an image of a person is present; and if an image of a person is determined to be present, determining whether the image of a person resembles one of a reference set of images of individuals.

One advantage of the invention is that it is fast, relatively simple and works well in a constrained environment, i.e., an environment for which the associated image remains relatively constant except for the coming and going of people. In addition, the invention determines whether a selected portion of an image actually contains an image of a face. If it is determined that the selected image portion contains an image of a face, the invention then determine which one of a reference set of known faces the detected face image most resembles. If the detected face image is not present among the reference set, the invention reports the presence of a unknown person in the audience. The invention has the ability to discriminate face images from images of other objects.

Other advantages and features will become apparent from the following description of the preferred embodiment and from the claims.

DESCRIPTION OF THE PREFERRED EMBODIMENT

STRUCTURE AND OPERATION

Figure 1:
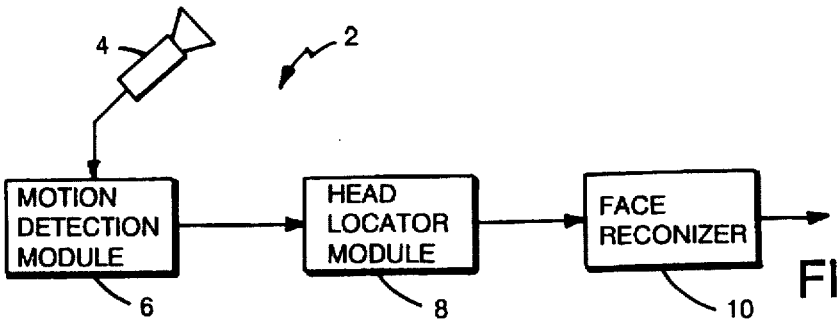
FIG. 1 is a block diagram of a face recognition system.

Referring to FIG. 1, in an audience monitoring system 2, a video camera 4, which is trained on an area where members of a viewing audience generally sit to watch the TV, sends a sequence of video image frames to a motion detection module 6. Video camera 4, which may, for example, be installed in the home of a family that has volunteered to participate in a study of public viewing habits, generates images of TV viewing audience. Motion detection module 6 processes the sequence of image frames to identify regions of the recorded scene that contain motion, and thus may be evidence of the presence of a person watching TV. In general, motion detection module 6 accomplishes this by comparing successive frames of the image sequence so as to find those locations containing image data that changes over time. Since the image background (i.e., images of the furniture and other objects in the room) will usually remain unchanged from frame to frame, the areas of movement will generally be evidence of the presence of a person in the viewing audience.

When movement is identified, a head locator module 8 selects a block of the image frame containing the movement and sends it to a face recognition module 10 where it is analyzed for the presence of recognizable faces. Face recognition module 10 performs two functions. First, it determines whether the image data within the selected block resembles a face. Then, if it does resemble a face, module 10 determines whether the face is one of a reference set of faces. The reference set may include, for example, the images of faces of all members of the family in whose house the audience monitoring system has been installed.

To perform its recognition functions, face recognizer 10 employs a multi-dimensional representation in which face images are characterized by a set of eigenvectors or "eigenfaces". In general, according to this technique, each image is represented as a vector (or a point) in very high dimensional image space in which each pixel of the image is represented by a corresponding dimension or axis. The dimension of this image space thus depends upon the size of the image being represented and can become very large for any reasonably sized image. For example, if the block of image data is N pixels by N pixels, then the multi-dimensional image space has dimension $N^2$. The image vector which represents the N×N block of image data in this multi-dimensional image space is constructed by simply concatenating the rows of the image data to generate a vector of length $N^2$.

Face images, like all other possible images, are represented by points within this multi-dimensional image space. The distribution of faces, however, tends to be grouped within a region of the image space. Thus, the distribution of faces of the reference set can be characterized by using principal component analysis. The resulting principal components of the distribution of faces, or the eigenvectors of the covariance matrix of the set of face images, defines the variation among the set of face images. These eigenvectors are typically ordered, each one accounting for a different amount of variation among the face images. They can be thought of as a set of features which together characterize the variation between face images within the reference set. Each face image location within the multi-dimensional image space contributes more or less to each eigenvector, so that each eigenvector represents a sort of ghostly face which is referred to herein as an eigenface.

Each individual face from the reference set can be represented exactly in terms of a linear combination of M non-zero eigenfaces. Each face can also be approximated using only the M' "best" faces, i.e., those that have the largest eigenvalues, and which therefore account for the most variance within the set of face images. The best M' eigenfaces span an M'-dimensional subspace (referred to hereinafter as "face space") of all possible images.

Figure 2:
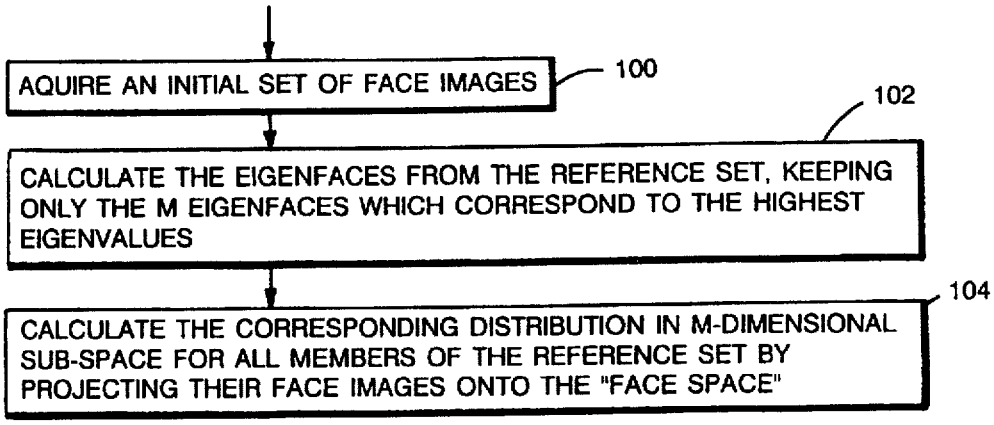
FIG. 2 is a flow diagram of an initialization procedure for the face recognition module.

This approach to face recognition involves the initialization operations shown in FIG. 2 to "train" recognition module 10. First, a reference set of face images is obtained and each of the faces of that set is represented as a corresponding vector or point in the multi-dimensional image space (step 100). Then, using principal component analysis, the distribution of points for the reference set of faces is characterized in terms of a set of eigenvectors (or eigenfaces) (step 102). If a full characterization of the distribution of points is performed, it will yield $N^2$ eigenfaces of which M are non-zero. Of these, only the M' eigenfaces corresponding to the highest eigenvalues are chosen, where $M' < M << N^2$. This subset of eigenfaces is used to define a subspace (or face space) within the multidimensional image space. Finally, each member of the reference set is represented by a corresponding point within face space (step 104). For a given face, this is accomplished by projecting its point in the higher dimensional image space onto face space.

If additional faces are added to the reference set at a later time, these operations are repeated to update the set of eigenfaces characterizing the reference set.

Figure 3:
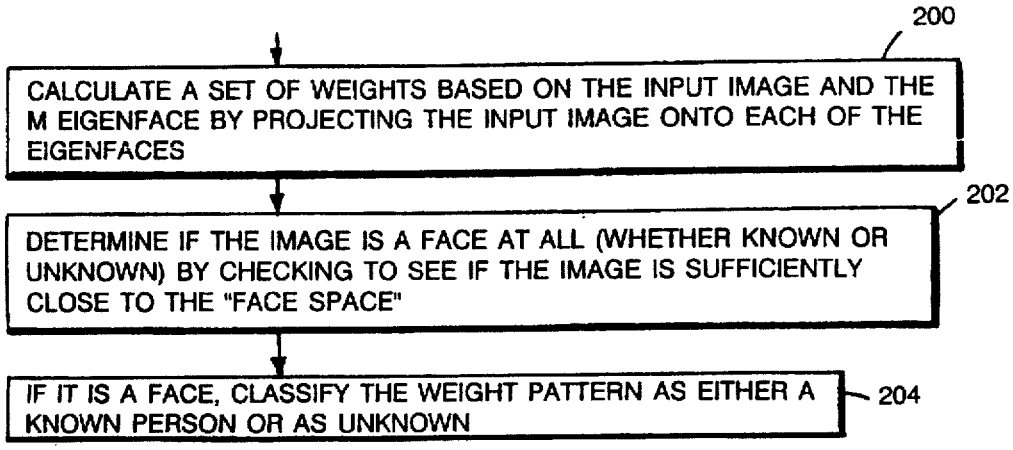
FIG. 3 is a flow diagram of the operation of the face recognition module.

After face recognition module 10 is initialized, it implements the steps shown in FIG. 3 to recognize face images supplied by face locator module 8. First, face recognition module 10 projects the input image (i.e., the image presumed to contain a face) onto face space by projecting it onto each of the M' eigenfaces (step 200). Then, module 10 determines whether the input image is a face at all (whether known or unknown) by checking to see if the image is sufficiently close to "face space" (step 202). That is, module 10 computes how far the input image in the multi-dimensional image space is from the face space and compares this to a preselected threshold. If the computed distance is greater than the preselected threshold, module 10 indicates that it does not represent a face image and motion detection module 6 locates the next block of the overall image which may contain a face image.

If the computed distance is sufficiently close to face space (i.e., less than the preselected threshold), recognition module 10 treats it as a face image and proceeds with determining whose face it is (step 206). This involves computing distances between the projection of the input image onto face space and each of the reference face images in face space. If the projected input image is sufficiently close to any one of the reference faces (i.e., the computed distance in face space is less than a predetermined distance), recognition module 10 identifies the input image as belonging to the individual associated with that reference face. If the projected input image is not sufficently close to any one of the reference faces, recognition module 10 reports that a person has been located but the identity of the person is unknown.

The mathematics underlying each of these steps will now be described in greater detail.

Calculating Eigenfaces

Let a face image I(x,y) be a two-dimensional N by N array of (8-bit) intensity values. The face image is represented in the multi-dimensional image space as a vector of dimension $N^2$. Thus, a typical image of size 256 by 256 becomes a vector of dimension 65,536, or, equivalently, a point in 65,536-dimensional image space. An ensemble of images, then, maps to a collection of points in this huge space.

Images of faces, being similar in overall configuration, are not randomly distributed in this huge image space and thus can be described by a relatively low dimensional subspace. Using principal component analysis, one identifies the vectors which best account for the distribution of face images within the entire image space. These vectors, namely, the "eigenfaces", define the "face space". Each vector is of length $N^2$, describes an N by N image, and is a linear combination of the original face images of the reference set.

Let the training set of face images be $\Gamma_1, \Gamma_2, \Gamma_3, \ldots, \Gamma_m$. The average face of the set is defined by $$\Psi=(M)^{-1}\Sigma_n\Gamma_n, \tag{1}$$

where the summation is from n=1 to M. Each face differs from the average by the vector $\Phi_i=\Gamma_i-\Psi$. This set of very large vectors is then subject to principal component analysis, which seeks a set of M orthonormal vectors, $u_n$, which best describes the distribution of the data. The kth vector, $u_k$, is chosen such that:

$$\lambda_k=(M)^{-1}\Sigma_n(u_k^T\Phi_n)^2 \tag{2}$$

is a maximum, subject to:

$$u_l^Tu_k=\delta_{lk}=\begin{cases}1, \text{ if } l=k\\ 0, \text{ otherwise}\end{cases} \tag{3}$$

The vectors $u_k$ and scalars $\lambda_k$ are the eigenvectors and eigenvalues, respectively, of the covariance matrix $$\begin{aligned} C &= (M)^{-1}\sum_n \phi_n\phi_n^T \\ &= AA^T \end{aligned} \tag{4}$$

where the matrix $A=[\Phi_1\ \Phi_2 \ldots \Phi_M]$. The matrix C, however, is $N^2$ by $N^2$, and determining the $N^2$ eigenvectors and eigenvalues can become an intractable task for typical image sizes.

If the number of data points in the face space is less than the dimension of the overall image space (namely, if, $M<N^2$), there will be only M−1, rather than $N^2$, meaningful eigenvectors. (The remaining eigenvectors will have associated eigenvalues of zero.) One can solve for the $N^2$-dimensional eigenvectors in this case by first solving for the eigenvectors of an M by M matrix—e.g. solving a 16×16 matrix rather than a 16,384 by 16,384 matrix—and then taking appropriate linear combinations of the face images $\Phi_i$. Consider the eigenvectors $v_i$ of $A^TA$ such that:

$$A^TAv_i=\mu_iv_i \tag{5}$$

Premultiplying both sides by A, yields:

$$AA^TAv_i=\mu_iAv_i \tag{6}$$

from which it is apparent that $Av_i$ are the eigenvectors of $C=AA^T$.

Following this analysis, it is possible to construct the M by M matrix $L=A^TA$, where $L_{mn}=\Phi_m^T\Phi_n$, and find the M eigenvectors, $v_l$, of L. These vectors determine linear combinations of the M training set face images to form the eigenfaces $u_l$:

$$u_l=\sum_{k=1}^{M} v_{lk}\phi_k,\ l=1,\ldots,M. \tag{7}$$

With this analysis the calculations are greatly reduced, from the order of the number of pixels in the images ($N^2$) to the order of the number of images in the training set (M). In practice, the training set of face images will be relatively small ($M<<N^2$), and the calculations become quite manageable. The associated eigenvalues provide a basis for ranking the eigenvectors according to their usefulness in characterizing the variation among the images.

In practice, a smaller M' is sufficient for identification, since accurate construction of the image is not a requirement. In this framework, identification becomes a pattern recognition task. The eigenfaces span an M'-dimensional subspace of the original $N^2$ image space. The M' significant eigenvectors of the L matrix are chosen as those with the largest associated eigenvalues. In test cases based upon M=16 face images, M'=7 eigenfaces were found to yield acceptable results, i.e., a level of accuracy sufficient for monitoring a TV audience for purposes of studying viewing habits and tastes.

A new face image (Γ) is transformed into its eigenface components (i.e., projected into "face space") by a simple operation, $$\omega_k=u_k^T(\Gamma-\Psi), \tag{8}$$

for k=1, . . . , M'. This describes a set of point-by-point image multiplications and summations, operations which may be performed at approximately frame rate on current image processing hardware.

The weights form a vector $\Omega^T=[\omega_1\omega_2 \ldots \omega_{M'}]$ that describes the contribution of each eigenface in representing the input face image, treating the eigenfaces as a basis set for face images. The vector may then be used in a standard pattern recognition algorithm to find which of a number of pre-defined face classes, if any, best describes the face. The simplest method for determining which face class provides the best description of an input face image is to find the face class k that minimizes the Euclidian distance $$\epsilon_k=\|(\Omega-\Omega_k)\|^2, \tag{9}$$

where $\Omega_k$ is a vector describing the kth face class. The face classes $\Omega_i$ are calculated by averaging the results of the eigenface representation over a small number of face images (as few as one) of each individual. A face is classified as belonging to class k when the minimum $\epsilon_k$ is below some chosen threshold $\theta_\epsilon$. Otherwise the face is classified as "unknown", and optionally used to create a new face class.

Because creating the vector of weights is equivalent to projecting the original face image onto the low-dimensional face space, many images (most of them looking nothing like a face) will project onto a given pattern vector. This is not a problem for the system, however, since the distance ε between the image and the face space is simply the squared distance between the mean-adjusted input image $\Phi=\Gamma-\Psi$ and $\Phi_f=[\epsilon\omega_k\mu_k]\Sigma\omega_k\mu_k$, its projection onto face space (where the summation is over k from 1 to M'):

$$\epsilon^2=\|\Phi-\Phi_f\|^2 \tag{10}$$

Thus, there are four possibilities for an input image and its pattern vector: (1) near face space and near a face class; (2) near face space but not near a known face class; (3) distant from face space and near a face class; and (4) distant from face space and not near a known face class.

In the first case, an individual is recognized and identified. In the second case, an unknown individual is present. The last two cases indicate that the image is not a face image. Case three typically shows up as a false positive in most other recognition systems. In the described embodiment, however, the false recognition may be detected because of the significant distance between the image and the subspace of expected face images.

Summary of Eigenface Recognition Procedure

To summarize, the eigenfaces approach to face recognition involves the following steps:

1. Collect a set of characteristic face images of the known individuals. This set may include a number of images for each person, with some variation in expression and in lighting. (Say four images of ten people, so M=40.)

2. Calculate the (40×40) matrix L, find its eigenvectors and eigenvalues, and choose the M' eigenvectors with the highest associated eigenvalues. (Let M'=10 in this example.)

3. Combine the normalized training set of images according to Eq. 7 to produce the (M'=10) eigenfaces $u_k$.

4. For each known individual, calculate the class vector $\Omega_k$ by averaging the eigenface pattern vectors $\Omega$ (from Eq. 9) calculated from the original (four) images of the individual. Choose a threshold $\theta_\epsilon$ which defines the maximum allowable distance from any face class, and a threshold $\theta_f$ which defines the maximum allowable distance from face space (according to Eq. 10).

5. For each new face image to be identified, calculate its pattern vector $\Omega$, the distances $\epsilon_i$ to each known class, and the distance $\epsilon$ to face space. If the distance $\epsilon>\theta_f$, classify the input image as not a face. If the minimum distance $\epsilon_k\leqq\theta_\epsilon$ and the distance $\epsilon\leqq\theta_1$, classify the input face as the individual associated with class vector $\Omega_k$. If the minimum distance $\epsilon_k>\theta\epsilon$ and $\epsilon\leqq\theta_1$, then the image may be classified as "unknown", and optionally used to begin a new face class.

6. If the new image is classified as a known individual, this image may be added to the original set of familiar face images, and the eigenfaces may be recalculated (steps 1–4). This gives the opportunity to modify the face space as the system encounters more instances of known faces.

In the described embodiment, calculation of the eigenfaces is done offline as part of the training. The recognition currently takes about 400 msec running rather inefficiently in Lisp on a Sun 4, using face images of size 128×128. With some special-purpose hardware, the current version could run at close to frame rate (33 msec).

Designing a practical system for face recognition within this framework requires assessing the tradeoffs between generality, required accuracy, and speed. If the face recognition task is restricted to a small set of people (such as the members of a family or a small company), a small set of eigenfaces is adequate to span the faces of interest. If the system is to learn new faces or represent many people, a larger basis set of eigenfaces will likely be required.

Motion Detection And Head Tracking

Figure 4:
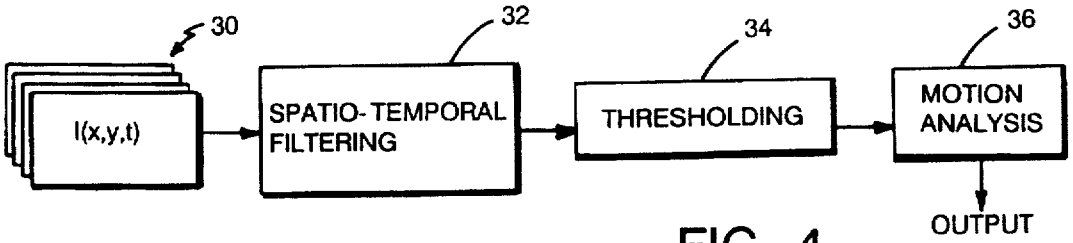
FIG. 4 is a block diagram of a motion detection system for locating faces within a sequence of images.

In the described embodiment, motion detection module 6 and head locator module 8 locates and tracks the position of the head of any person within the scene viewed by video camera 4 by implementing the tracking algorithm depicted in FIG. 4. A sequence of image frames 30 from video camera 4 first passes through a spatio-temporal filtering module 32 which accentuates image locations which change with time. Spatio-temporal filtering module 32 identifies the locations of motion by performing a differencing operation on successive frames of the sequence of image frames. In the output of the spatio-temporal filter module 32, a moving person "lights up" whereas the other areas of the image containing no motion appear as black.

The spatio-temporal filtered image passes to a thresholding module 34 which produces a binary motion image identifying the locations of the image for which the motion exceeds a preselected threshold. That is, it locates the areas of the image containing the most motion. In all such areas, the presence of a person is postulated.

A motion analyzer module 36 analyzes the binary motion image to watch how "motion blobs" change over time to decide if the motion is caused by a person moving and to determine head position. A few simple rules are applied, such as "the head is the small upper blob above a larger blob (i.e., the body)", and "head motion must be reasonably slow and contiguous" (i.e., heads are not expected to jump around the image erratically).

The motion image also allows for an estimate of scale. The size of the blob that is assumed to be the moving head determines the size of the subimage to send to face recognition module 10 (see FIG. 1). This subimage is rescaled to fit the dimensions of the eigenfaces.

Using "Face Space" To Locate The Face

Face space may also be used to locate faces in single images, either as an alternative to locating faces from motion (e.g. if there is too little motion or many moving objects) or as a method of achieving more precision than is possible by use of motion tracking alone.

Typically, images of faces do not change radically when projected into the face space; whereas, the projection of non-face images appear quite different. This basic idea may be used to detect the presence of faces in a scene. To implement this approach, the distance [e] $\epsilon$ between the local subimage and face space is calculated at every location in the image. This calculated distance from face space is then used as a measure of "faceness". The result of calculating the distance from face space at every point in the image is a "face map" $\epsilon(x,y)$ in which low values (i.e., the dark areas) indicate the presence of a face.

Direct application of Eq. 10, however, is rather expensive computationally. A simpler, more efficient method of calculating the face map $\epsilon(x,y)$ is as follows.

To calculate the face map at every pixel of an image I(x,y), the subimage centered at that pixel is projected onto face space and the projection is then subtracted from the original subimage. To project a subimage $\Gamma$ onto face space, one first subtracts the mean image (i.e., $\Psi$), resulting in $\Phi=\Gamma-\Psi$. With $\Phi_f$ being the projection of $\Phi$ onto face space, the distance measure at a given image location is then:

$$\begin{aligned}\epsilon^2 &= \|\phi - \phi_f\|^2 \\ &= (\phi - \phi_f)^T(\phi - \phi_f) \\ &= \phi^T\phi - \phi^T\phi_f + \phi_f^T(\phi - \phi_f) \\ &= \phi^T\phi - \phi_f^T\phi_f\end{aligned} \tag{11}$$

since $\Phi_f \perp (\Phi - \Phi_f)$. Because $\Phi_f$ is a linear combination of the eigenfaces ($\Phi_f = \Sigma_i \omega_i u_i$) and the eigenfaces are orthonormal vectors, $$\Phi_f^T \Phi_f = \Sigma_i \omega_i^2 \tag{12}$$

and $$\epsilon^2(x,y) = \Phi^T(x,y)\,\Phi(x,y) - \Sigma \omega_i^2(x,y) \tag{13}$$

where $\epsilon(x,y)$ and $\omega_i(x,y)$ are scalar functions of image location, and $\Phi(x,y)$ is a vector function of image location.

The second term of Eq. 13 is calculated in practice by a correlation with the L eigenfaces:

$$\begin{aligned}\sum_1 \omega_i^2(x, y) &= \sum_i \phi^T(x, y) u_i \\ &= \sum_i (\Gamma(x, y) - \psi)^T u_i \\ &= \sum_i (\Gamma^T(x, y) u_i - \psi^T u_i) \\ &= \sum_i (I(x, y) + u_i - \psi^T u_i)\end{aligned} \tag{14}$$

where $\otimes$ the correlation operator. The first term of Eq. 13 becomes $$\begin{aligned}\phi^T(x, y)\phi(x, y) &= (\Gamma(x, y) - \psi)^T(\Gamma(x, y) - \psi) \\ &= \Gamma^T(x, y)\Gamma(x, y) - 2\psi^T(x, y) + \psi^T\psi \\ &= \Gamma^T(x, y)\Gamma(x, y) - 2\Gamma(x, y) + \psi + \psi^T\psi\end{aligned} \tag{15}$$

so that $$\epsilon^2(x, y) = \Gamma^T(x, y)\Gamma(x, y) - 2\Gamma^T\Gamma(x, y) + \otimes\psi + \psi^T\psi + \sum_i (\Gamma(x, y) + u_i - \psi + u_i) \tag{15}$$

Since the average face $\Psi$ and the eigenfaces $u_i$ are fixed, the terms $\Psi^T\Psi$ and $\Psi \otimes u_i$ may be computed ahead of time.

Thus, the computation of the face map involves only L+1 correlations over the input image and the computation of the first term $\Gamma^T(x,y)\Gamma(x,y)$. This is computed by squaring the input image I(x,y) and, at each image location, summing the squared values of the local subimage.

Scale Invariance

Experiments reveal that recognition performance decreases quickly as the head size, or scale, is mis-judged. It is therefore desirable for the head size in the input image must be close to that of the eigenfaces. The motion analysis can give an estimate of head size, from which the face image is rescaled to the eigenface size.

Another approach to the scale problem, which may be separate from or in addition to the motion estimate, is to use multiscale eigenfaces, in which an input face image is compared with eigenfaces at a number of scales. In this case the image will appear to be near the face space of only the closest scale eigenfaces. Equivalently, the input image (i.e., the portion of the overall image selected for analysis) can be scaled to multiple sizes and the scale which results in the smallest distance measure to face space used.

Other embodiments are within the following claims. For example, although the eigenfaces approach to face recognition has been presented as an information processing model, it may also be implemented using simple parallel computing elements, as in a connectionist system or artificial neural network.

What is claimed is:

1. A recognition system for identifying members of an audience, the system comprising:

an imaging system which generates an image of the audience;

a selector module for selecting a portion of said generated image;

means for representing a reference set of images of individuals as a set of eigenvectors in a multi-dimensional image space;

a detection means which determines whether the selected image portion contains an image that can be classified as an image of a person, said detection means including means for representing said selected image portion as an input vector in said multi-dimensional image space and means for computing the distance between a point identified by said input vector and a multi-dimensional subspace defined by said set of eigenvectors, wherein said detection means uses the computed distance to determine whether the selected image portion contains an image that can be classified as an image of a person; and a recognition module responsive to said detection means for determining whether a detected image of a person identified by said detection means resembles one of the reference set of images of individuals.

2. The recognition system of claim 1 wherein said detection means further comprises a thresholding means for determining whether an image of a person is present by comparing said computed distance to a preselected threshold.

3. The recognition system of claim 1 wherein said [selection means] *selector module* comprises a motion detector for identifying the selected portion of said image by detector motion.

4. The recognition system of claim 3 wherein said [selection means] *selector module* further comprises a locator module for locating the portion of said image corresponding to a face of the person based on motion detected by said motion detector.

5. The recognition system of claim 1 wherein said image of a person is an image of a person's face and wherein said reference set comprises images of faces of said individuals.

6. The recognition system of claim 1 wherein said recognition module comprises means for representing each member of said reference set as a corresponding point in said subspace.

7. The recognition system of claim 6 wherein the location of each point in subspace associated with a corresponding member of said reference set is determined by projecting a vector associated with that member onto said subspace.

8. The recognition system of claim 7 wherein said recognition module further comprises means for projecting said input vector onto said subspace.

9. The recognition system of claim 8 wherein said recognition module further comprises means for selecting a particular member of said reference set and means for computing a distance within said subspace between a point identified by the projection of said input vector onto said subspace and the point in said subspace associated with said selected member.

10. The recognition system of claim 8 wherein said recognition module further comprises means for determining for each member of said reference set a distance in subspace between the location associated with that member in subspace and the point identified by the projection of said input vector onto said subspace.

11. The recognition system of claim 10 wherein said image of a person is an image of a person's face and wherein said reference set comprises images of faces of said individuals.

12. A method for identifying members of an audience, the method comprising:

generating an image of the audience;

selecting a portion of said generated image;

representing a reference set of images of individuals as a set of eigenevectors in a multi-dimensional image space;

representing said selected image portion as an input vector in said multi-dimensional image space;

computing the distance between a point identified by said input vector and a multi-dimensional subspace defined by said set of eigenvectors;

using the computed distance to determine whether the selected image portion contains an image that can be classified as an image of a person; and if it is determined that the selected image contains an image that can be classified as an image of a person determining whether said image of a person resembles one of a reference set of images of individuals.

13. The method of claim 12 further comprising the step of determining which one, if any, of the members of said reference set said image of a person resembles.

14. The method of claim 12 wherein the image of the audience is a sequence of image frames and wherein the method further comprises detecting motion within the sequence of image frames and wherein the selected image portion is determined on the basis of the detected motion.

15. The method of claim 12 wherein the step of determining whether the selected image portion contains an image that can be classified as an image of a person further comprises comparing said computed distance to a preselected threshold.

16. The method of claim 15 wherein the step of determining whether said image of a person resembles a member of said reference set comprises representing each member of said reference set as a corresponding point in said subspace.

17. The method of claim 16 wherein the step of determining whether said image of a person resembles a member of said reference set further comprises determining the location of each point in subspace associated with a corresponding member of said reference set by projecting a vector associated with that member onto said subspace.

18. The method of claim 17 wherein the step of determining whether said image of a person resembles a member of said reference set further comprises projecting said input vector onto said subspace.

19. The method of claim 18 wherein the step of determining whether said image of a person resembles a member of said reference set further comprises selecting a member of said reference set and computing a distance within said subspace between a point identified by the projection of said input vector onto said subspace and the point in said subspace associated with said selected member.

20. The method of claim 18 wherein the step of determining whether said image of a person resembles a member of said reference set further comprises determining for each member of said reference set a distance in subspace between the location for that member in subspace and the point identified by the projection of said input vector onto said subspace.

21. The method of claim 20 wherein said image of a person is an image of a person's face and wherein said reference set comprises images of faces of said individuals.

*22. A recognition system comprising:*

*an imaging system which generates an image;*

*a selector module for selecting a portion of said generated image;*

*means for representing a reference set of images of individuals as a set of eigenvectors in a multi-dimensional image space;*

*a detection means which determines whether the selected image portion contains an image that can be classified as an image of a person, said detection means including means for representing said selected image portion as an input vector in said multi-dimensional image space and means for computing the distance between a point identified by said input vector and a multi-dimensional subspace defined by said set of eigenvectors, wherein said detection means uses the computed distance to determine whether the selected image portion contains an image that can be classified as an image of a person; and*

*a recognition module responsive to said detection means for determining whether a detected image of a person identified by said detection means resembles one of the reference set of images of individuals.*

*23. The recognition system of claim 22 wherein said detection means further comprises a thresholding means for determining whether an image of a person is present by comparing said computed distance to a preselected threshold.*

*24. The recognition system of claim 22 wherein said image of a person is an image of a person's face and wherein said reference set comprises images of faces of said individuals.*

*25. The recognition system of claim 22 wherein said recognition module comprises means for representing each member of said reference set as a corresponding point in said subspace.*

*26. The recognition system of claim 25 wherein the location of each point in subspace associated with a corresponding member of said reference set is determined by projecting a vector associated with that member onto said subspace.*

*27. The recognition system of claim 26 wherein said recognition module further comprises means for projecting said input vector onto said subspace.*

*28. The recognition system of claim 27 wherein said recognition module further comprises means for selecting a particular member of said reference set and means for computing a distance within said subspace between a point identified by the projection of said input vector onto said subspace and the point in said subspace associated with said selected member.*

*29. The recognition system of claim 27 wherein said recognition module further comprises means for determining for each member of said reference set a distance in subspace between the location associated with that member in subspace and the point identified by the projection of said input vector onto said subspace.*

*30. The recognition system of claim 24 wherein said means for representing said reference set includes means for*

*adding a member to said reference set by protecting into said subspace an input vector having a computed distance indicative of an image of a face.*

*31. A method comprising:*

*generating an image;*

*selecting a portion of said generated image;*

*representing a reference set of images of faces of individuals as a set of eigenvectors in a multi-dimensional image space;*

*representing said selected image portion as an input vector in said multi-dimensional image space;*

*computing the distance between a point identified by said input vector and a multi-dimensional subspace defined by said set of eigenvectors;*

*using the computed distance to determine whether the selected image portion contains an image that can be classified as an image of a person's face; and*

*if it is determined that the selected image contains an image that can be classified as an image of a person's face, determining whether said image of a person's face resembles one of a reference set of images of faces of individuals.*

*32. The method of claim 31 further comprising the step of determining which one, if any, of the members of said reference set said image of a person's face resembles.*

*33. The method of claim 31 wherein the step of determining whether the selected image portion contains an image that can be classified as an image of a person's face further comprises comparing said computed distance to a preselected threshold.*

*34. The method of claim 33 wherein the step of determining whether said image of a person's face resembles a member of said reference set comprises representing each member of said reference set as a corresponding point in said subspace.*

*35. The method of claim 34 wherein the step of determining whether said image of a person's face resembles a member of said reference set further comprises determining the location of each point in subspace associated with a corresponding member of said reference set by projecting a vector associated with that member onto said subspace.*

*36. The method of claim 35 wherein the step of determining whether said image of a person's face resembles a member of said reference set further comprises projecting said input vector onto said subspace.*

*37. The method of claim 36 wherein the step of determining whether said image of a person's face resembles a member of said reference set further comprises determining for each member of said reference set a distance in subspace between the location for that member in subspace and the point identified by the projection of said input vector onto said subspace.*

* * * * *